US012059332B2

(12) United States Patent
Enz et al.

(10) Patent No.: US 12,059,332 B2
(45) Date of Patent: Aug. 13, 2024

(54) PROCESS FOR MAKING ABSORBENT ARTICLES WITH EXTENDED LEG ELASTICS

(71) Applicant: Kimberly-Clark Worldwide, Inc., Neenah, WI (US)

(72) Inventors: David J. Enz, Neenah, WI (US); James P. King, Farr West, UT (US); Sarah A. Kleuskens, Neenah, WI (US); Pat Abney, Menasha, WI (US); Kevin Dolan, Pine River, WI (US); Qianxiang Feng, Neenah, WI (US); Andrew T. Hammond, Grand Chute, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1062 days.

(21) Appl. No.: 16/489,011

(22) PCT Filed: Feb. 28, 2017

(86) PCT No.: PCT/US2017/019909
§ 371 (c)(1),
(2) Date: Aug. 27, 2019

(87) PCT Pub. No.: WO2018/160166
PCT Pub. Date: Sep. 7, 2018

(65) Prior Publication Data
US 2019/0388282 A1    Dec. 26, 2019

(51) Int. Cl.
*A61F 13/49*    (2006.01)
*A61F 13/494*    (2006.01)
*A61F 13/56*    (2006.01)

(52) U.S. Cl.
CPC .. *A61F 13/49017* (2013.01); *A61F 13/49011* (2013.01); *A61F 13/49413* (2013.01); *A61F 13/5633* (2013.01); *A61F 2013/49088* (2013.01)

(58) Field of Classification Search
CPC .......... A61F 13/49011; A61F 13/49017; A61F 13/49413; A61F 13/5633; A61F 2013/49088
See application file for complete search history.

(56) References Cited

U.S. PATENT DOCUMENTS 5,525,175 A  *  6/1996  Blenke .............. A61F 13/15593
                                                  604/385.24
5,683,531 A  *  11/1997 Roessler ........... A61F 13/15593
                                                  604/385.24
(Continued)

FOREIGN PATENT DOCUMENTS

CN         1946548 A     4/2007
CN       101426462 A     5/2009
(Continued)

OTHER PUBLICATIONS

International Search Report and Written Opinion for PCT/US2017/019909 dated Nov. 27, 2017, 9 pages.
(Continued)

*Primary Examiner* — Michele Kidwell
(74) *Attorney, Agent, or Firm* — Dority & Manning, P.A.

(57) ABSTRACT

An absorbent article is described that includes leg elastics that form the outermost edges of the product. The leg elastics can include an increased number of elastomeric strands and can extend outboard of the chassis. In this manner, the leg elastics can form a proper seal with the legs of the wearer without interference and can be visually inspected by a caregiver. Placing the leg elastics outboard of the chassis also provides for an efficient manner of producing the
(Continued)

garment by attaching multiple elastic components to the garment along a vertical bonding seam.

22 Claims, 11 Drawing Sheets

(56) References Cited

U.S. PATENT DOCUMENTS

| | | | |
|---|---|---|---|
| 6,531,015 B1 | 11/2003 | Gardner | |
| 8,062,279 B2 | 11/2011 | Miyamoto | |
| 8,771,449 B2 | 7/2014 | Takino et al. | |
| 8,821,469 B2 | 9/2014 | Otsubo et al. | |
| 8,978,163 B2 | 3/2015 | Kinoshita et al. | |
| 2003/0079330 A1* | 5/2003 | Stopher | B65H 39/14 29/430 |
| 2003/0116257 A1* | 6/2003 | Franklin | A61F 13/49017 156/161 |
| 2003/0135192 A1* | 7/2003 | Guralski | A61F 13/15747 604/391 |
| 2012/0157958 A1* | 6/2012 | Tenorio | A61F 13/49015 604/385.25 |
| 2014/0148323 A1* | 5/2014 | Brown | A61F 13/15609 493/380 |
| 2014/0274644 A1 | 9/2014 | Thorson et al. | |
| 2015/0126952 A1 | 5/2015 | Tenorio et al. | |
| 2020/0000648 A1* | 1/2020 | Kleuskens | A61F 13/4902 |

FOREIGN PATENT DOCUMENTS

| | | |
|---|---|---|
| CN | 101674792 A | 3/2010 |
| CN | 101784716 A | 7/2010 |
| CN | 102574389 A | 7/2012 |
| CN | 102781391 A | 11/2012 |
| CN | 103260574 A | 8/2013 |
| CN | 105073079 A | 11/2015 |
| CN | 105434113 A | 3/2016 |
| CN | 105636564 A | 6/2016 |
| CN | 105705125 A | 6/2016 |
| JP | H10504988 A | 5/1998 |
| JP | 2009291330 | 12/2009 |
| JP | 2014012211 | 1/2014 |
| WO | WO2001/092013 A1 | 12/2001 |
| WO | WO2010016785 | 2/2010 |
| WO | WO2012080871 | 6/2012 |
| WO | WO2016/138466 A1 | 9/2016 |

OTHER PUBLICATIONS

Korean Office Action Corresponding to Application No. 1020197026082 dated Aug. 31, 2020.
Australian Office Action Corresponding to Application No. 2017401507 dated Sep. 7, 2022.

* cited by examiner

PROCESS FOR MAKING ABSORBENT ARTICLES WITH EXTENDED LEG ELASTICS

RELATED APPLICATIONS

The present application is based upon and claims priority to PCT International Patent Application No. PCT/US20171019909, filed on Feb. 28, 2017, which is incorporated herein by reference.

BACKGROUND

Many disposable garments, such as diapers, incontinence articles, training pants, feminine hygiene products, hospital gowns, bandages, and the like include various elastic portions that are intended to give the garments form fitting properties. For example, many disposable diapers include elastic members positioned around the waist of the garment and leg elastics which are intended to surround the legs of the wearer. In addition, diapers can also include elasticized, longitudinally extending barrier flaps which encircle the upper thighs of the wearer. The above elastic portions are intended to not only make the garment more comfortable to wear, but are also used to inhibit the leakage of body fluids from the absorbent article.

In addition, some disposable diapers made in the past have included elastic fastener tabs that are typically joined to the rear portion of the article and are configured to releasably attach to the front of the article, partially encircling a users waist when being worn.

The amount of stretch and elasticity present in the absorbent article in the transverse direction can have a significant impact upon the perceived comfort and fit of the garment. For example, if the elastic portions of the article only elongate when relatively high forces are exerted on the article, consumers may perceive that the product will not fit correctly and may not provide room for any movement without irritation from the product. If the article, on the other hand, stretches under relatively low amounts of force, consumers may perceive that the product fit will degrade during wear and may result in leakage.

One problem faced by garment makers is the ability to easily incorporate into the garment the different elastic portions, especially at high production speeds. Typically, extra materials are needed in order to incorporate elastics into the garment. For example, an extended length of material is typically used in order to support and accommodate the placement of leg elastics that surround the legs of the wearers. This extra material has a tendency to bunch together and form undulations due to the presence of the leg elastics and have the appearance of a ruffle that extends beyond the edge of the leg elastics and surrounds the legs of the wearer. During use, this excess material or ruffle can fold inward during donning of the product or while the product is being worn. When the excess material or ruffle becomes folded within the product or under the leg elastic, the absorbent article may experience leg leakage which is very undesirable. In view of the above, a need exists for an improved absorbent article that is perceived by consumers to have the best BM and urine leakage protection. A need also exists for a method and process for incorporating elastics, such as leg elastics into an absorbent article in a more elegant and/or efficient manner. A need also exists for an absorbent article that eliminates excess material and a ruffle that overlaps the leg elastics.

SUMMARY

In general, the present disclosure is directed to a method for producing disposable absorbent articles and particularly absorbent articles having specially designed leg elastics that surround the leg openings of the article. In one embodiment, the method includes the steps of forming a chassis that has a first longitudinal edge opposite a second longitudinal edge. First and second leg elastics are attached to the chassis along the longitudinal edges in a manner such that the leg elastics extend outboard of the chassis and can extend from a top edge of the chassis to a bottom edge of the chassis. A first vertical bonding seam can be formed along the first longitudinal edge and a second vertical bonding seam can be formed along the second longitudinal edge for not only attaching the leg elastics to the chassis, but also for attaching elastic side panels, elastic containment flaps, and at least one waist elastic. Each vertical bonding seam can include a thermal point bonded pattern that extends from the top edge to the bottom edge of the chassis.

In one embodiment, for instance, the method includes the steps of forming a first leg elastic along a first longitudinal edge of a moving first substrate and forming a second leg elastic along a second and opposite longitudinal edge of the moving substrate. Each leg elastic comprises at least one elastic member, such as a plurality of elastomeric strands. The first leg elastic extends outboard of the first longitudinal edge of the first substrate and the second leg elastic extends outboard of the second longitudinal edge. A first side panel is joined to the first leg elastic and a second side panel is joined to the second leg elastic. The first side panel is associated with a first fastening device and the second side panel is associated with a second fastening device. A plurality of absorbent assemblies are attached to the first substrate. A second substrate is then joined to the first substrate such that the absorbent assemblies are positioned between the first substrate and the second substrate. Joining the first substrate to the second substrate forms a chassis of the absorbent article. The first substrate, for instance, may comprise a bodyside liner while the second substrate may comprise an outer cover material or vice versus. After the two substrates are joined together, the substrates can be cut into a plurality of discrete absorbent articles.

As described above, the first leg elastic can be attached to the substrate along a first vertical bonding seam while the second leg elastic can be joined to the substrate along a second vertical bonding seam. Each leg elastic can comprise an elastic laminate structure that can be attached to the substrate or integral with the substrate. In one embodiment, each vertical bonding seam comprises a plurality of columns of offset bond points that extend from a top edge to a bottom edge of the absorbent article. In one embodiment, each vertical bonding seam comprises a column of bond points wherein the bond points have a higher density over the side panels sufficient not only to attach the side panels to the leg elastics but also to deaden the one or more elastic members in the leg elastics.

The present disclosure is also directed to a method of manufacturing absorbent articles by forming a chassis by enclosing an absorbent structure in between a bodyside liner and an outer cover material. The chassis includes a first longitudinal edge spaced from a second longitudinal edge that extend from a top edge of the chassis to a bottom edge of the chassis. A first leg elastic is attached along the first longitudinal edge of the chassis to form a first vertical bond seam and a second leg elastic is attached along a second longitudinal edge to form a second longitudinal bond seam.

Each longitudinal bond seam extends from the top edge to the bottom edge of the chassis and wherein the leg elastics extend outboard of the longitudinal edges of the chassis.

A first side panel is attached to the leg elastics adjacent the bottom edge of the article and a second elastic side panel is attached to the second leg elastic adjacent the bottom edge of the article. In accordance with the present disclosure, the elasticity of each leg elastic is deadened along a top portion of each leg elastic adjacent the top edge and along a bottom portion of each leg elastic adjacent the bottom edge.

Each side panel can be attached only to a respective leg elastic. Alternatively, each side panel may overlap the chassis in an amount less than about 6 mm, such as in an amount less than about 3 mm.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
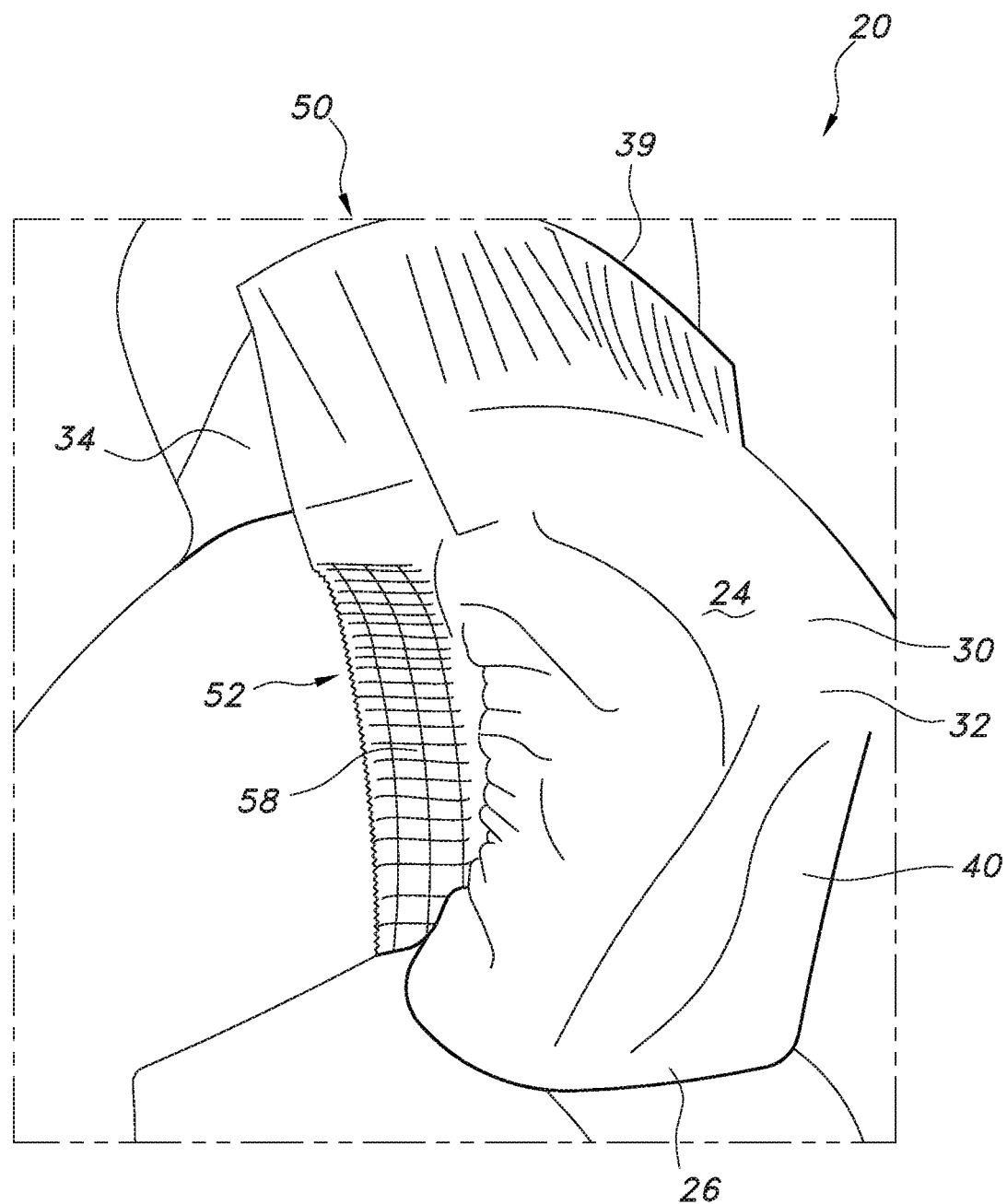
FIG. 1 is a rear perspective view of one embodiment of a garment made in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

The present disclosure is generally directed to an absorbent article having leg elastics form the outermost portion of the article along the legs of the wearer. The garments constructed in accordance with the present disclosure can comprise, for instance, disposable articles, such as diapers, training pants, swim pants, feminine hygiene products, adult incontinence products, and the like.

Locating the leg elastics so as to extend out beyond the chassis of the absorbent article and form the outermost edges of the garment can provide numerous advantages and benefits. For example, the leg elastics are in a better position to form a leak-proof bond with the leg of the wearer. The design not only prevents leaks but minimizes the bridging of BM movement. In essence, placing the leg elastics outboard of the product chassis improves overall functional performance of the leg elastics. By making the leg elastics the outermost edge of the product also allows for caregivers to view the leg elastics and ensure that they have formed a good seal around the legs of the wearer.

Placing the leg elastics outboard of the product chassis also allows for the manufacture of the product without any additional materials used in the past in order to secure the leg elastics to the product. For instance, products can be made without including a piece of material that forms a leg ruffle, which can interfere with the ability of the leg elastic to form a proper seal. The garment of the present disclosure also provides a premium wholistic look.

Another advantage to the absorbent article configuration of the present disclosure is that the absorbent article can be constructed in an efficient manner. For example, placing the leg elastics outboard of the chassis allows for the product to be made from a more rectangular blank as opposed to an hourglass shape. In this manner, two parallel and linear vertical bonding seams can be formed into the product during manufacture that can be used to connect all of the elastic elements to the product. For instance, the vertical bonding seams can be used to not only attach the leg elastics to the product but can also be used to attach fasteners associated with elastic side panels, elastic containment flaps, one or more waist elastics, and the like.

Figure 2:
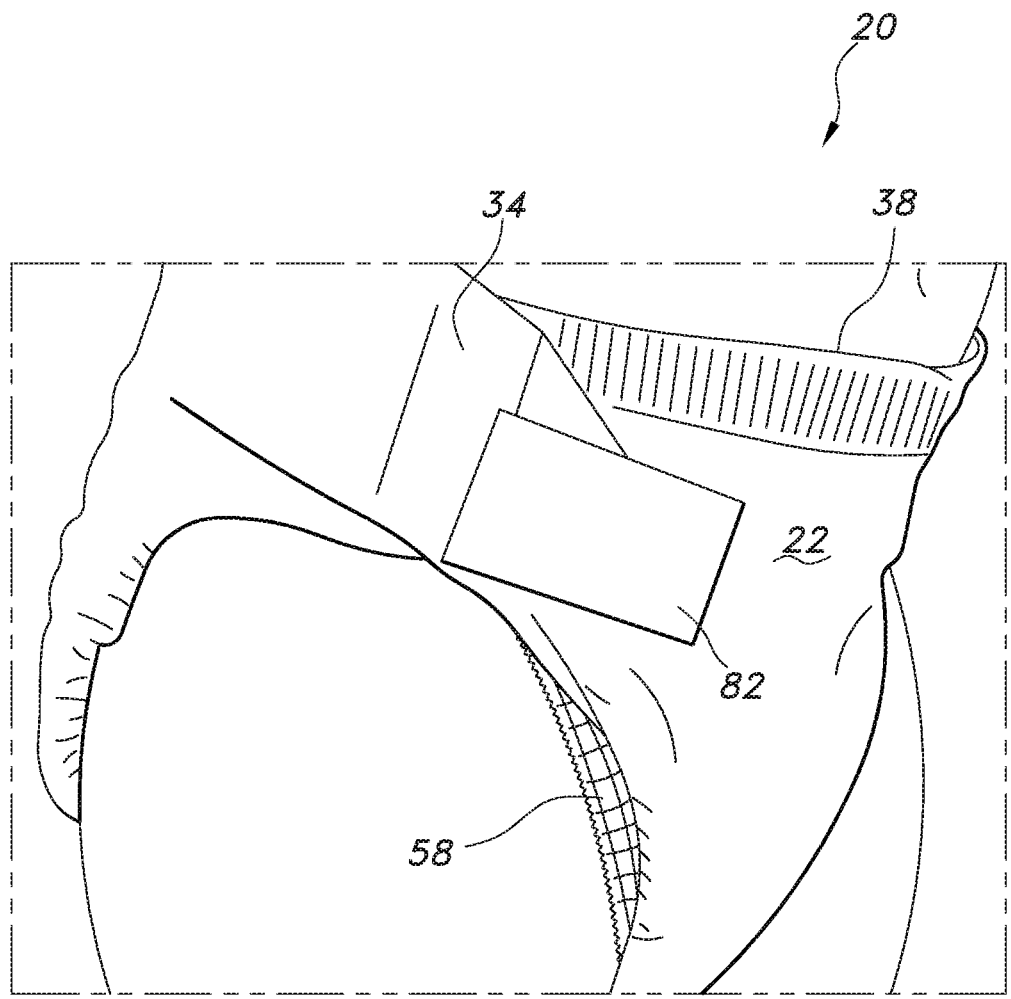
FIG. 2 is a front perspective view of the garment illustrated in FIG. 1.

Referring to FIGS. 1 and 2, for exemplary purposes, an absorbent article 20 that may be made in accordance with the present disclosure is shown. The absorbent article 20 may or may not be disposable. It is understood that the present disclosure is suitable for use with various other garments intended for personal wear, including but not limited to diapers, training pants, swim pants, feminine hygiene products, incontinence products, medical garments, and the like without departing from the scope of the present disclosure.

Figure 3:
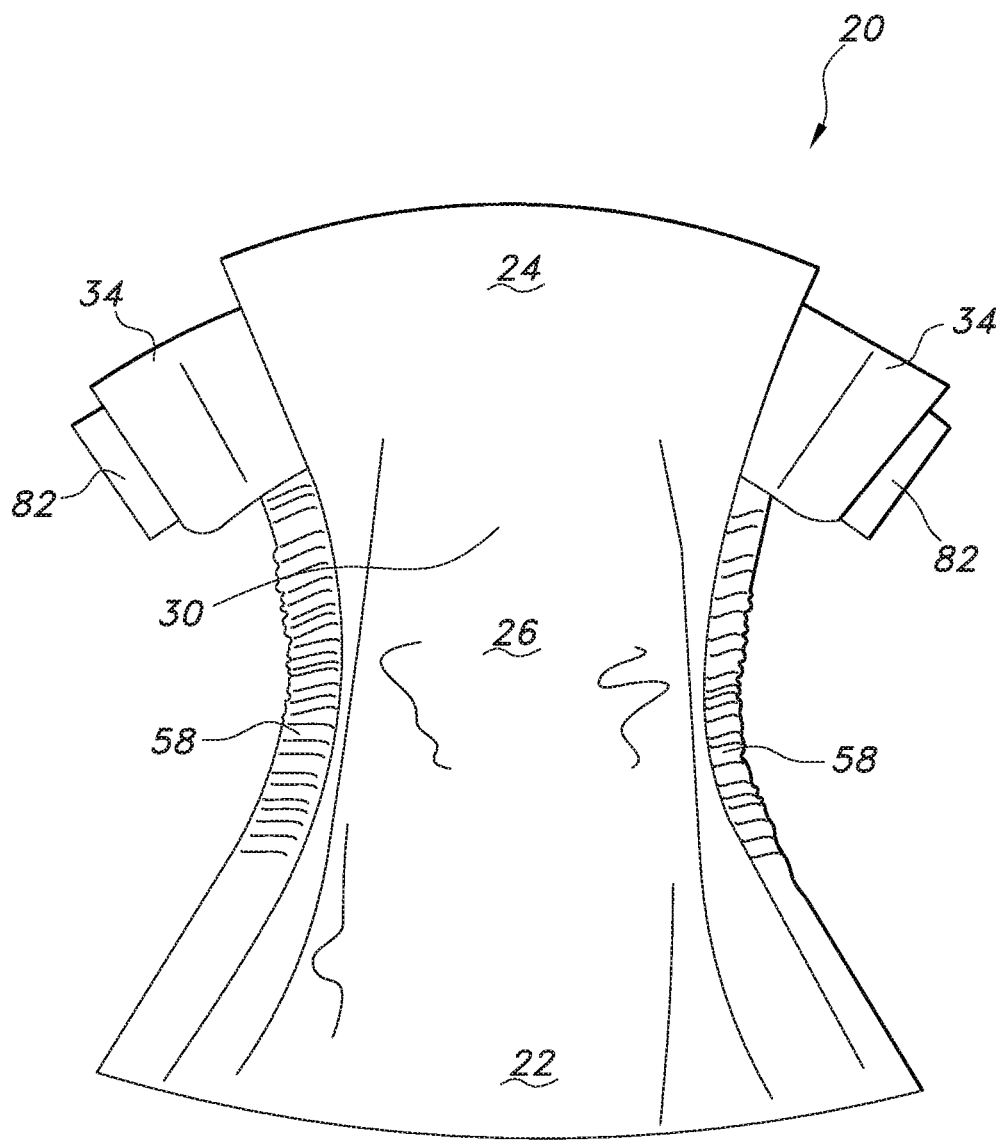
FIG. 3 is a plan view of the garment shown in FIG. 1 with the article in an unfastened, unfolded and laid flat condition showing the surface of the article that faces away from the wearer.
Figure 4:
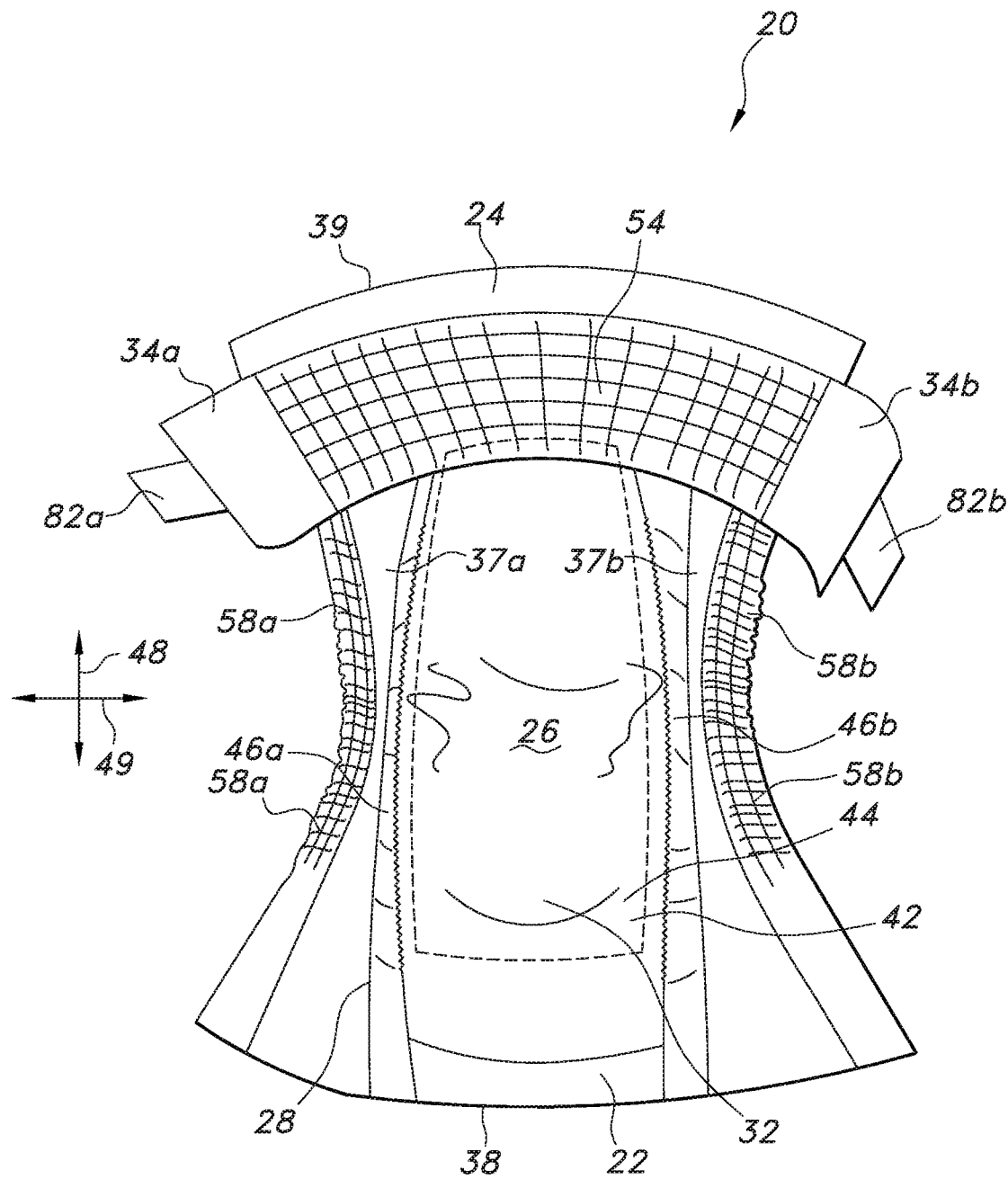
FIG. 4 is a plan view similar to FIG. 3 showing the surface of the garment that faces the wearer when worn.

A diaper 20 is representatively illustrated in FIG. 1 in a fastened condition. The diaper 20 shown in FIGS. 1 and 2 is also represented in FIGS. 3 and 4 in an opened and unfolded state. Specifically, FIG. 3 is a plan view illustrating the exterior side of the diaper 20, while FIG. 4 illustrates the interior side of the diaper 20. As shown in FIGS. 3 and 4, the diaper 20 defines a longitudinal direction 48 that extends from the front of the article when worn to the back of the article. Opposite to the longitudinal direction 48 is a lateral direction 49.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20, which when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of longitudinally opposite waist edges, respectively designated front waist edge 38 and back waist edge 39.

The illustrated diaper 20 includes a chassis 32 that, in this embodiment, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam and a back waist seam. The liner 42 can be generally adapted, i.e., positioned relative to the other components of the article 20, to be disposed toward the wearer's skin during wear of the absorbent article. The chassis 32 may further include an absorbent structure 44 (shown in phantom) disposed between the outer cover 40 and the bodyside liner 42 for absorbing liquid body exudates exuded by the wearer.

The outer cover 40, the inner liner 42 and the absorbent structure 44 may be made from many different materials depending upon the particular application and the desired result. All three layers, for instance, may be extendable and/or elastic. Further, the stretch properties of each layer may vary in order to control the overall stretch properties of the product.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded card webs or foams provided by elastomeric or polymeric materials. The outer cover 40, for instance, can be a single layer of a liquid impermeable material, or alternatively can be a multi-layered laminate structure in which at least one of the layers is liquid impermeable. In other embodiments, however, it should be understood that the outer cover may be liquid permeable. In this embodiment, for instance, the absorbent article may contain an interior liquid barrier layer.

In one embodiment, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

Alternatively, the outer cover 40 may include a woven or non-woven fibrous web layer which has been totally or partially constructed or treated to impart the desired levels of liquid impermeability to selected regions that are adjacent or proximate the absorbent structure. For example, the outer cover 40 may include a gas-permeable, non-woven fabric layer laminated to a polymer film layer which may or may not be gas-permeable. Other examples of fibrous, cloth-like outer cover 40 materials can include a stretch thinned or stretch thermal laminate material composed of a 0.6 mil (0.015 mm) thick polypropylene blown film and a 0.7 osy (23.8 gsm) polypropylene spunbond material (2 denier fibers).

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., USA, and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, SXM 9394, and Favor 9543 superabsorbents are available from DeGussa Superabsorbers.

After being formed or cut into a desired shape, the absorbent web material may be wrapped or encompassed by a suitable tissue or meltblown web or the like wrap sheet that aids in maintaining the integrity and shape of the absorbent structure 44.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene.

In one embodiment, the absorbent structure 44 may also be elastomeric. For this purpose, the absorbent web material can include elastomeric fibers in an amount which is at least a minimum of about 2 wt %. The amount of elastomeric fibers can alternatively be at least about 3 wt %, and can optionally be at least about 5 wt % to provide improved performance. In addition, the amount of elastomeric fibers can be not more than about 60 wt %. Alternatively, the amount of elastomeric fibers can be not more than about 45 wt %, and optionally, can be not more than about 30 wt % to provide improved benefits. These values may impact the absorbent structure 44 by affecting the desired levels of stretchability and structural stability without excessively degrading the physical properties or the liquid-management properties of the absorbent structure. An absorbent web material with an excessively low proportion of elastomeric fibers may be insufficiently stretchable, and a web material with an excessively high proportion of elastomeric fibers may exhibit an excessive degradation of its absorbency functionalities, such as poor intake, poor distribution, poor retention of liquid.

In some embodiments, the absorbent article 20 may further include a surge management layer (not shown) which may be optionally located adjacent the absorbent structure and attached to various components in the article 20 such as the absorbent structure or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure.

In accordance with the present disclosure, the absorbent article 20 further includes a plurality of elastic components that are incorporated into the product. Notably, the absorbent article 20 can include leg elastics, one or more waist elastics, elastic containment flaps, and/or elastic side panels that are associated with fasteners. As used herein, the chassis 32 is defined as the absorbent article absent the above elastic components. Thus, the chassis 32 can comprise those portions of the outer cover 40, the bodyside liner 42, and the absorbent structure 44 that do not make up the elastic components.

In the embodiment illustrated in FIG. 4, the absorbent article 20 includes two leg elastics 58a and 58b, a pair of opposing elastic containment flaps 46a and 46b, a pair of opposing elastic side panels 34a and 34b, and a back waist elastic member 54. As shown particularly in FIGS. 1-4, the absorbent article 20 made in accordance with the present disclosure includes leg elastics 58 that extend outboard of the chassis 32. As shown in FIG. 1, for instance, the leg elastic 58 can be positioned in the garment so that it is clearly visible when being worn and can comprise the outermost edge of the product, especially within the crotch region. In this manner, no other extraneous materials can interfere with the leg elastic 58 for forming a proper seal against the leg. In addition, a caregiver can visually inspect the leg elastics 58 in order to verify that the leg elastic has made a proper leakproof seal against the leg.

As will be described in greater detail below, the leg elastics 58a and 58b as shown in FIG. 4 can be formed of any suitable elastic material. For instance, the leg elastics 58 can include sheets, strands, or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one embodiment, the leg elastics 58 comprise a plurality of dry-spun coalesced multifilament spandex elastomeric threads. Of particular advantage, because the leg elastics 58 are positioned as the outermost edges of the absorbent article 20, a greater number of elastomeric strands can be easily incorporated into the leg elastics for ensuring a leakproof fit with the leg of a wearer. For instance, each leg elastic 58a and 58b can be comprised of greater than two elastomeric strands, such as greater than three elastomeric strands, such as greater than four elastomeric strands and generally less than about ten elastomeric strands, such as less than about eight elastomeric strands, such as less than about six elastics strands.

Another advantage to having the leg elastics 58 form the outermost edges of the absorbent article 20 is that the absorbent article can be produced with a rectangular chassis 32 and/or a rectangular outer cover 40 and/or a bodyside liner 42. As shown in FIG. 4, due to the retractive forces of the leg elastics, the leg elastics 58 naturally form a shape on the absorbent article that conforms to the legs of the wearer. Consequently, placing the leg elastics outboard of the chassis provides for not only an elegant design but also a very efficient design. For example, the design of the present disclosure requires no extra material to support the leg elastics thereby eliminating a ruffle around the legs of the wearer which can not only interfere with the ability of the leg elastics to provide a leakproof fit, but also provide cost savings by reducing the width of the chassis. In addition, the chassis 32 or outer cover 40 can include a pair of opposing longitudinal edges 37a and 37b. The longitudinal edges 37 can be linear and parallel. In accordance with the present disclosure, the leg elastics 58, the side panels 34, and the containment flaps 46 can all be attached to the absorbent article along the longitudinal edges 37a and 37b forming linear and parallel vertical bonding seams. In this manner, the absorbent article 20 can be assembled very quickly and at high speeds without having to conduct separate maneuvering processes in order to place the elastic components in the article around edges with curved or complex configurations.

The chassis 32 is comprised of the outer cover 40 and the bodyside liner 42. In one embodiment, the outer cover 40 can include an outer layer superimposed with an inner layer that may comprise a liquid impermeable film. In accordance with the present disclosure, the outer cover layer can be wider than the liquid impermeable film in constructing the chassis 32. The outer cover layer is generally narrower than the edge of the leg elastics. In other words, the leg elastics extend outward beyond the edges of the outer cover layer. In one embodiment as will be described in greater detail below, however, the elastomeric strands that form the leg elastics can be directly adhered to the outer cover layer such that the leg elastics become integral with the outer cover layer.

The elasticized containment flaps 46 as shown in FIG. 4 define a partially unattached edge which assumes an upright configuration in at least the crotch region 26 of the diaper 20 to form a seal against the wearer's body. The containment flaps 46 can extend longitudinally along the entire length of the chassis 32 or may extend only partially along the length of the chassis.

The pair of opposing elastic side panels 34 are attached to the back region of the chassis 32. As shown particularly in FIGS. 1 and 2, the side panels 34 may be stretched around the waist and/or hips of a wearer in order to secure the garment in place. As shown in FIGS. 3 and 4, the elastic side panels are attached to the article along the pair of opposing longitudinal edges 37. The side panels 34 may be attached or bonded to the article using any suitable bonding technique. For instance, the side panels 34 may be joined to the chassis by adhesives, ultrasonic bonds, thermal bonds, or other conventional techniques.

In the embodiments shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 1 and 2, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the embodiments shown in the figures, the side panels are releasably attachable to the front region 22 of the article 20 by the fastening system. It should be understood, however, that in other embodiments the side panels may be permanently joined to the chassis 32 at each end. The side panels may be permanently bonded together, for instance, when forming a training pant or absorbent swimwear.

The fastening system 80 may include laterally opposite first fastening components 82 adapted for refastenable engagement to corresponding second fastening components. In the embodiment shown in the figures, the first fastening component 82 is located on the elastic side panels 34, while the second fastening component comprises the front region 22 of the chassis 32. In one aspect, a front or outer surface of each of the fastening components includes a plurality of engaging elements. The engaging elements of the first fastening components 82 are adapted to repeatedly engage and disengage corresponding engaging elements of the second fastening components to releasably secure the article 20 in its three-dimensional configuration. In the embodiment illustrated in FIG. 3, the fastening system includes a first fastening device 82a and a second fastening device 82b which may comprise hook fasteners. The second fastening component, on the other hand, may comprise an exterior surface of the outer cover material which is adapted to engage the hooks.

It should be understood, however, the fastening components may be any refastenable fasteners suitable for absorbent articles, such as adhesive fasteners, cohesive fasteners, mechanical fasteners, or the like.

In the embodiment shown in the figures, the fastening components 82a and 82b are attached to the corresponding side panels 34a and 34b along the edges. In this embodiment, the fastening components 82 are not elastic or extendable. In other embodiments, however, the fastening components may be integral with the side panels 34. For example, the fastening components may be directly attached to the side panels 34 on a surface thereof.

As shown, the absorbent article 20 may include various extensible waist members. These extensible waist members may also be elastic for providing elasticity around the waist opening. For example, as shown in FIG. 4, the absorbent article 20 can include a back waist elastic member 54. The waist elastic members are for providing the absorbent article with at least one form fitting property. The waist elastic members also prevent leakage of body fluids from the absorbent article.

When incorporating an elastomeric component, such as described above, into the absorbent article of the present disclosure, it is often desired that the elastomeric material form an elastic laminate with one or more other layers, such as foams, films, apertured films, and/or nonwoven webs. The elastic laminate generally contains layers that can be bonded together so that at least one of the layers has the characteristics of an elastic polymer. Examples of elastic laminates include, but are not limited to, stretch-bonded laminates and neck-bonded laminates.

As used herein, the term "stretch-bonded" refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the nonelastic layer is fully extended. One type of stretch-bonded laminate is disclosed, for example, in U.S. Pat. No. 4,720,415 to Vander Wielen et al., which is incorporated herein by reference. Other composite elastic materials are described and disclosed in U.S. Pat. No. 4,789,699 to Kieffer et al., U.S. Pat. No. 4,781,966 to Taylor, U.S. Pat. No. 4,657,802 to Morman, and U.S. Pat. No. 4,655,760 to Morman et al., all of which are incorporated herein by reference thereto.

As used herein, the term "neck-bonded" refers to an elastic member being bonded to a non-elastic member while the non-elastic member is extended in the machine direction creating a necked material. "Neck-bonded laminate" refers to a composite material having at least two layers in which one layer is a necked, non-elastic layer and the other layer is an elastic layer thereby creating a material that is elastic in the cross direction. Examples of neck-bonded laminates are such as those described in U.S. Pat. Nos. 5,226,992, 4,981,747, 4,965,122, and 5,336,545, all to Morman, all of which are incorporated herein by reference thereto.

In one embodiment, the elastic member can be a neck stretched bonded laminate. As used herein, a neck stretched bonded laminate is defined as a laminate made from the combination of a neck bonded laminate and a stretch bonded laminate. Examples of necked stretched bonded laminates are disclosed in U.S. Pat. Nos. 5,114,781 and 5,116,662, which are both incorporated herein by reference. Of particular advantage, a neck stretch bonded laminate is stretchable in the machine direction and in a cross machine direction.

In one particular embodiment, the elastic member comprises a stretch-bonded laminate. The stretch-bonded laminate can include elastic threads made from an elastomeric material sandwiched between two polypropylene spunbond layers. The elastic threads can be, for instance, made from a styrene-ethylene butylene-styrene block of polymer, such as KRATON G2740, available from Krayton Polymers, LLC. The stretch-bonded laminate, for instance, can have a basis weight of from about 0.5 osy to about 8 osy, and particularly from about 1.5 osy to about 3.5 osy.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 to Kinney, U.S. Pat. No. 3,341,394 to Kinney, U.S. Pat. No. 3,502,763 to Hartman, and U.S. Pat. No. 3,542,615 to Dobo et al., Spunbond fibers are generally not tacky when they are deposited on a collecting surface. Spunbond fibers are generally continuous and have average diameters (from a sample of at least 10) larger than 7 microns, and more particularly, between about 10 and 40 microns.

The above described elastic laminates can be used to construct any and all of the elastic components contained within the absorbent article 20.

Figure 5:
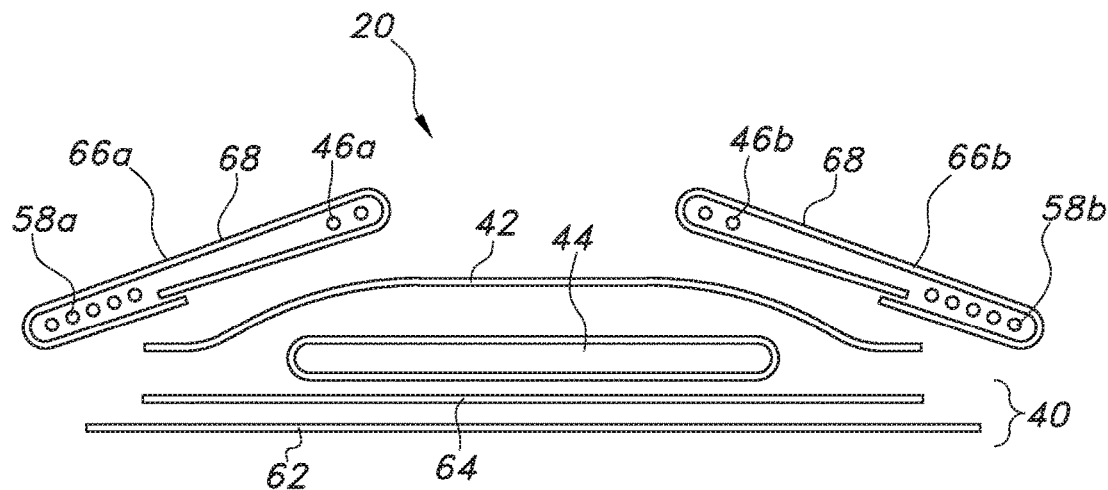
FIG. 5 is a cross-sectional view of one embodiment of a garment made in accordance with the present disclosure.
Figure 6:
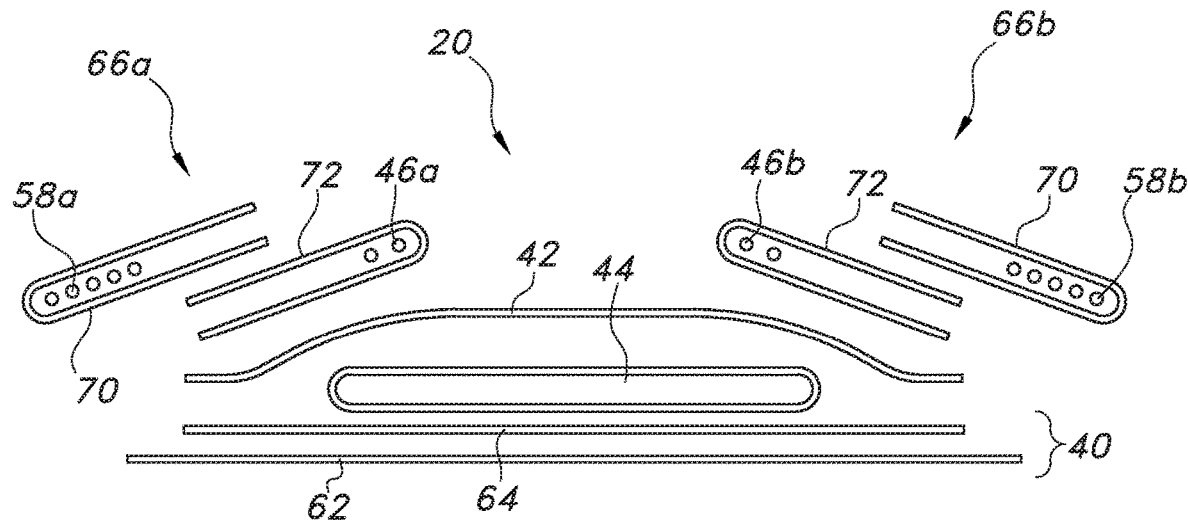
FIG. 6 is a cross-sectional view of another embodiment of a garment made in accordance with the present disclosure.
Figure 7:
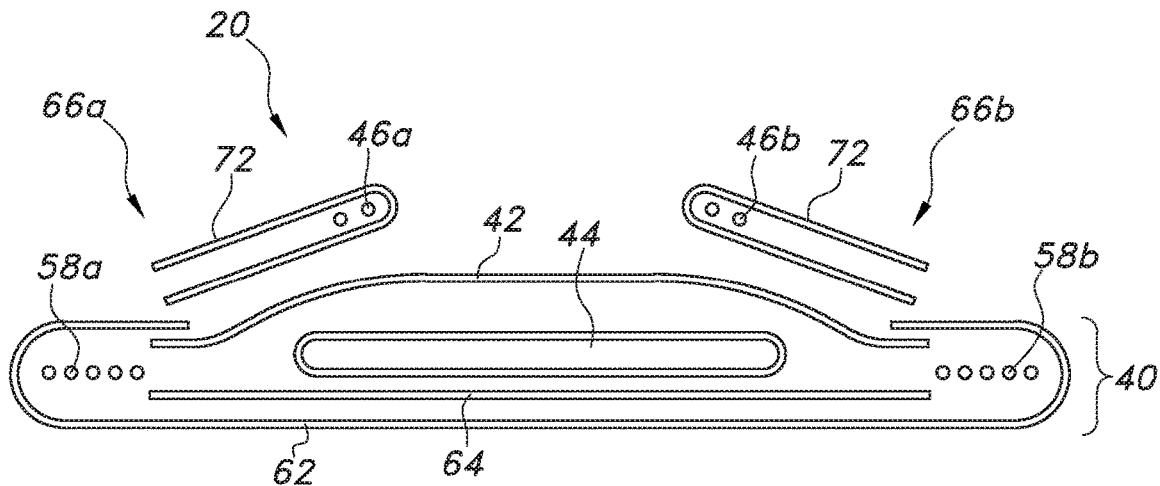
FIG. 7 is another cross-sectional view of a garment made in accordance with the present disclosure.

As described above, one aspect of absorbent articles made in accordance with the present disclosure is that the leg elastics 58 extend outboard of the chassis 32. In one embodiment, the leg elastics can extend the entire length of the absorbent article along the longitudinal edges 37 of the chassis 32. The chassis 32 can have a rectangular configuration allowing the leg elastics to be attached along a longitudinal and vertical line. In addition, the containment flaps 46 can be attached to the leg elastics 58 along the vertical line. Referring to FIGS. 5-7, different embodiments are shown for forming and constructing the leg elastics 58 and the elastic containment flaps 46.

Referring to FIG. 5, for instance, the absorbent article 20 includes a bodyside liner 42, an outer cover 40, and an absorbent structure 44 placed in between the bodyside liner and the outer cover. In this embodiment, the outer cover 40 comprises a first layer 62 superimposed with a second layer 64. As shown in FIG. 5, in one embodiment, the first layer 62, which may comprise a nonwoven web, can be wider than the second layer 64, which can comprise a liquid impermeable film. Alternatively, the first layer 62 can have the same width as the second layer 64. The first layer, for instance, may comprise a nonwoven web while the second layer may comprise a liquid impermeable film. In accordance with the present disclosure, the absorbent article 20 further includes a pair of opposing elastic laminate structures 66a and 66b. Each elastic laminate structure 66 comprises a first plurality of elastomeric strands that comprise the leg elastics 58a and 58b spaced from a second plurality of elastomeric strands that comprise the elastic containment flaps 46a and 46b. As shown, the elastic laminate structure 66 in this embodiment is formed by enclosing the first plurality of elastomeric strands and the second plurality of elastomeric strands within a web of material 68. A method for producing elastic laminate structures that may be used in accordance with the present disclosure is disclosed in U.S. Pat. No. 8,956,493, which is incorporated herein by reference. In the embodiment illustrated in FIG. 5, the elastomeric strands are completely enclosed within a single web of material 68. It should be understood, however, that in an alternative embodiment, the elastomeric strands are adhered to one side of the web of material and are not completely enclosed.

In the embodiment illustrated in FIG. 5, the elastic laminate structures 66a and 66b can be bonded to the chassis of the absorbent article at any suitable location. For instance, the elastic laminate structures 66a and 66b can be bonded to the liner 42, to the first layer 62 of the outer cover 40, to the second layer 64 of the outer cover 40 or can be bonded to all of the layers.

FIG. 6 is similar to FIG. 5 and like reference numerals have been used to indicate similar elements. In the embodiment illustrated in FIG. 6, each elastic laminate structure 66a and 66b is formed from two pieces of material joined together. For instance, the leg elastics 58a and 58b are formed by enclosing elastic filaments within a first web of material 70. The containment flaps 46a and 46b, on the other hand, are formed by enclosing elastic filaments within a second web of material 72. In order to form the elastic laminate structure 66, the leg elastic 58 is attached to the containment flap 46. The elastic laminate structures 66a and 66b are then bonded or attached to the chassis of the absorbent article 20 similar to FIG. 5. In the embodiment illustrated in FIG. 6, the containment flaps 46 are shown below the leg elastics 58. Alternatively, however, the leg elastics 58 can be positioned below the containment flaps 46. In the embodiment illustrated in FIG. 6, the leg elastics 58 can have a different elongation or dtx than the containment flaps 46.

Referring to FIG. 7, another embodiment of a configuration for showing the formation of leg elastics and containment flaps is illustrated. In the embodiment in FIG. 7, the outer cover 40 includes a first layer 62 superimposed with a second layer 64. The first layer 62 can have different material properties than the second layer 64. For instance, as described above, the first layer 62 can comprise a nonwoven web while the second layer 64 can comprise a liquid impermeable film. As shown, the first layer 62 is significantly wider than the second layer 64. In this manner, the leg elastics 58a and 58b can be formed by attaching elastomeric strands to the first layer 62 outside the edges of the second layer 64. Alternatively, some elastomeric strands can be attached to the first layer 62 while the remaining elastomeric strands can be attached to the second layer 64. In one embodiment, as shown in FIG. 7, the first layer 62 can be folded in order to enclose the elastomeric strands. The outer edge of the first layer 62 can then be bonded or attached to the bodyside liner 42, the second layer 64, or to both the bodyside liner 42 and the second layer 64. In the embodiment illustrated in FIG. 7, a portion of the first layer 62 of the outer cover 40 becomes integrated into the leg elastics 58 (and is no longer part of the chassis).

In another embodiment, the elastic laminate structure 66 comprising the containment flaps 46 and the leg elastics 58 can be wrapped around the bottom edge of the first layer 62 and the second layer 64. In this manner, some of the elastomeric strands would reside on the second layer 64 and some of the elastomeric strands would reside on the elastic laminate structure 66. In this embodiment, the first layer 62 can be narrower. In this configuration, adhesive can be applied to extend below the elastic side panels making the attachment stronger.

The containment flaps 46a and 46b in FIG. 7 are made similar to the containment flaps in FIG. 6. As shown, each containment flap 46 is formed by enclosing elastomeric strands within a web of material 72. In this manner, the elastic laminate structures 66a and 66b are formed by attaching together the containment flaps 46 with the leg elastics 58.

In the embodiments illustrated in FIGS. 5-7, the leg elastics 58 are shown containing five elastomeric strands. In general, the leg elastics will be made from at least three strands, such as at least four strands and can provide various advantages. By using an increased number of elastomeric strands, the leg elastics span the distance from the containment flaps to the outer product width for adequate bucketing and product coverage. Using at least three elastomeric strands to form the leg elastic provides sufficient elasticity around the legs which reduces sag in the crotch and provides for a better fit. Using an increased number of elastomeric strands also provides a wide band that can used as a visual cue for the caregiver to ensure that the leg elastics have formed a proper seal against the legs.

In the embodiments of FIGS. 5-7, the leg elastics (and optionally the containment flaps) can extend the entire length of the article from a top edge to a bottom edge. The elastomeric strands contained within the leg elastics can all have the same length and can also extend the entire length of the article from a top edge to a bottom edge. Alternatively, however, the elastomeric strands can have different lengths. For instance, as will be described in greater detail below, in one embodiment, the outermost elastomeric strands can be shorter than the innermost elastomeric strands. The outermost elastomeric strands, for instance, may extend from the back region to the crotch region and then terminate. This configuration may provide various advantages, such as a better fit.

The chassis can have a substantially rectangular shape allowing the leg elastics to be attached along the longitudinal edges 37 of the chassis. In one embodiment, vertical bonding seams can also be formed along the longitudinal edges 37 that are used to not only attach the leg elastics and the containment flaps, but can also be used to attach the elastic side panels. In this manner, all of the above elastic components are attached to the absorbent article along two parallel and linear bonding seams.

Figure 8:
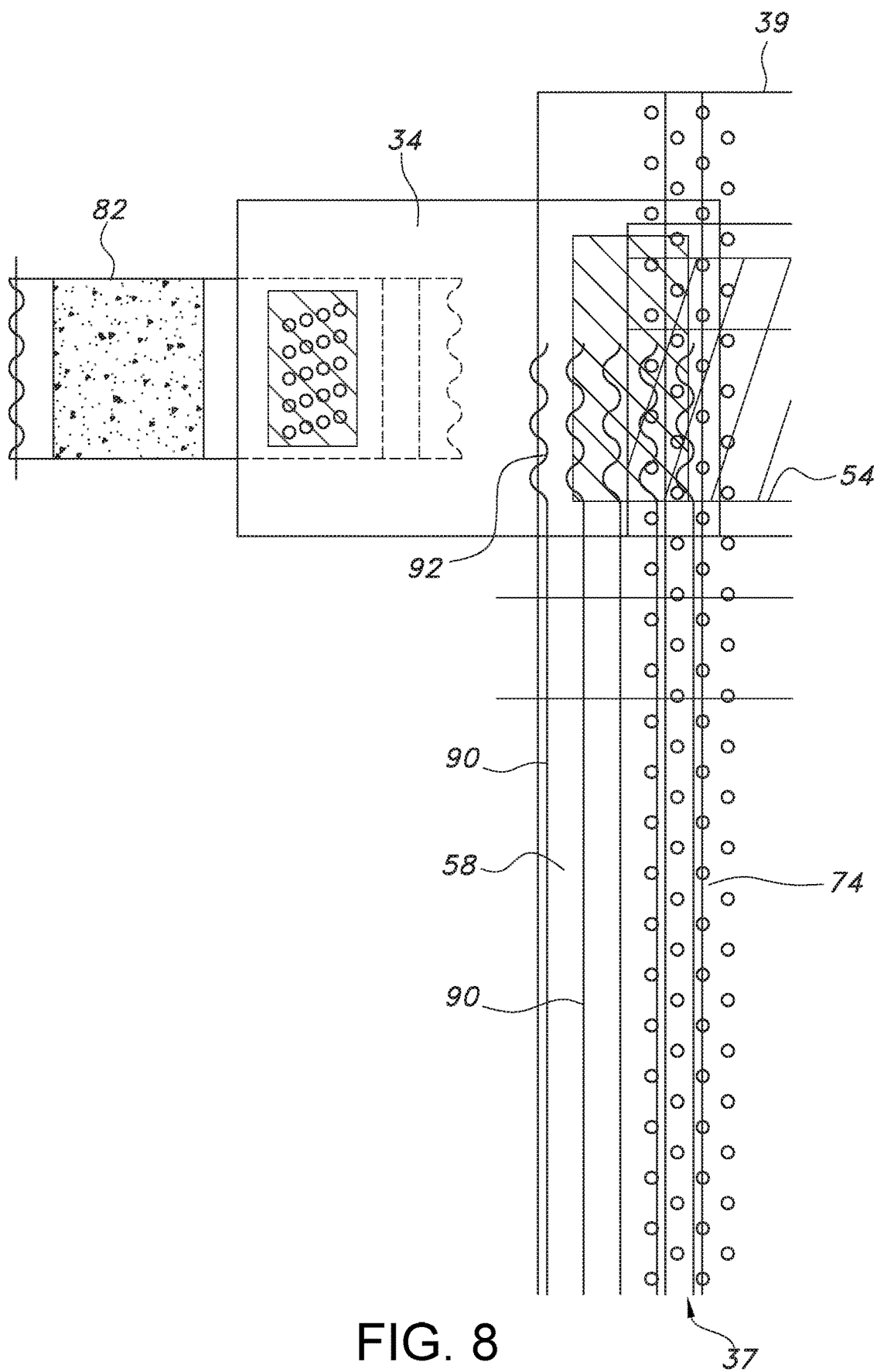
FIG. 8 is a plan view of a portion of a garment made in accordance with the present disclosure illustrating one embodiment of a vertical bonding seam for attaching components to the garment and severing elastics.
Figure 9:
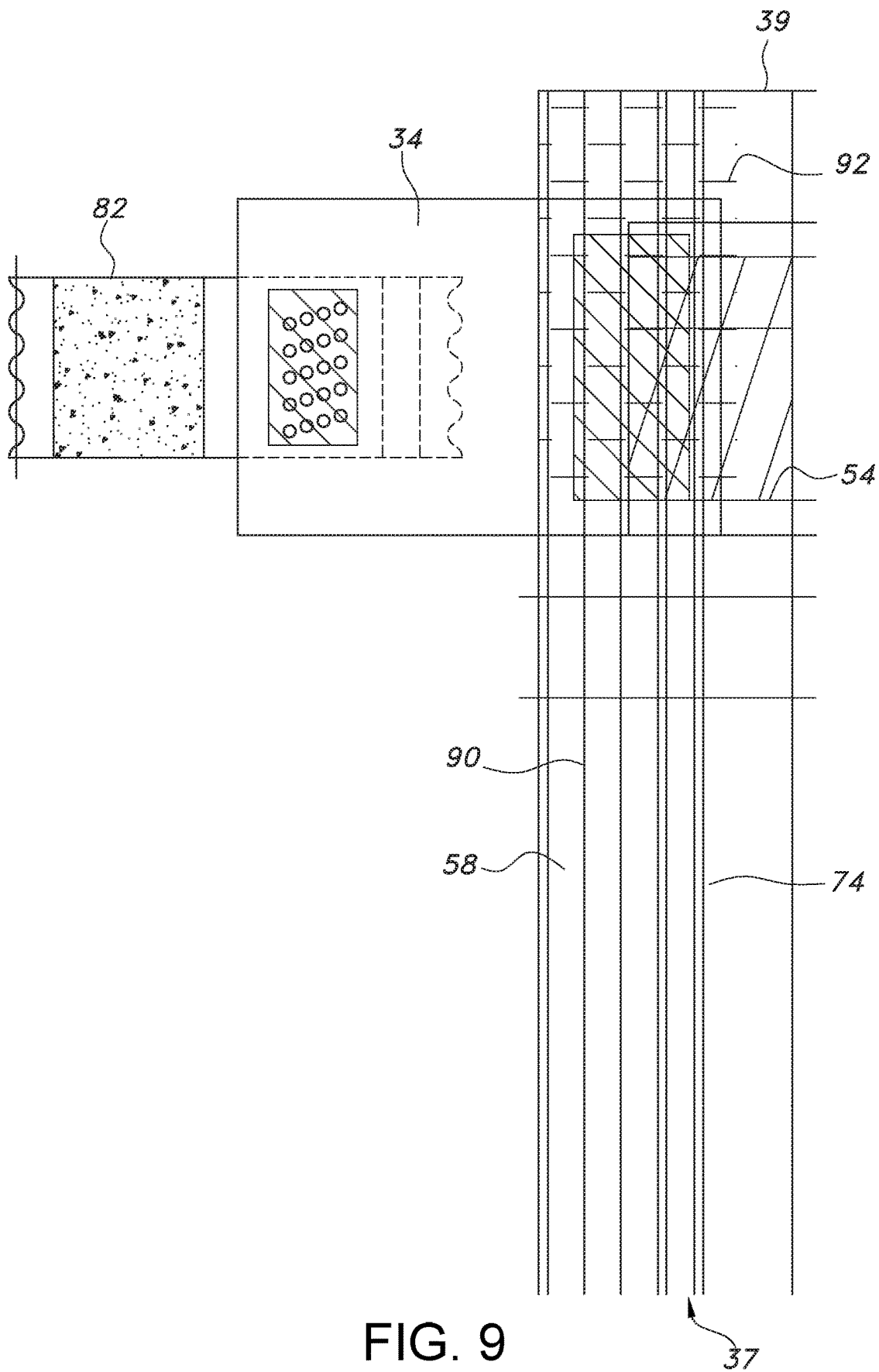
FIG. 9 is a plan view of a portion of a garment made in accordance with the present disclosure illustrating another embodiment of a vertical bonding seam for attaching components to the garment.
Figure 10:
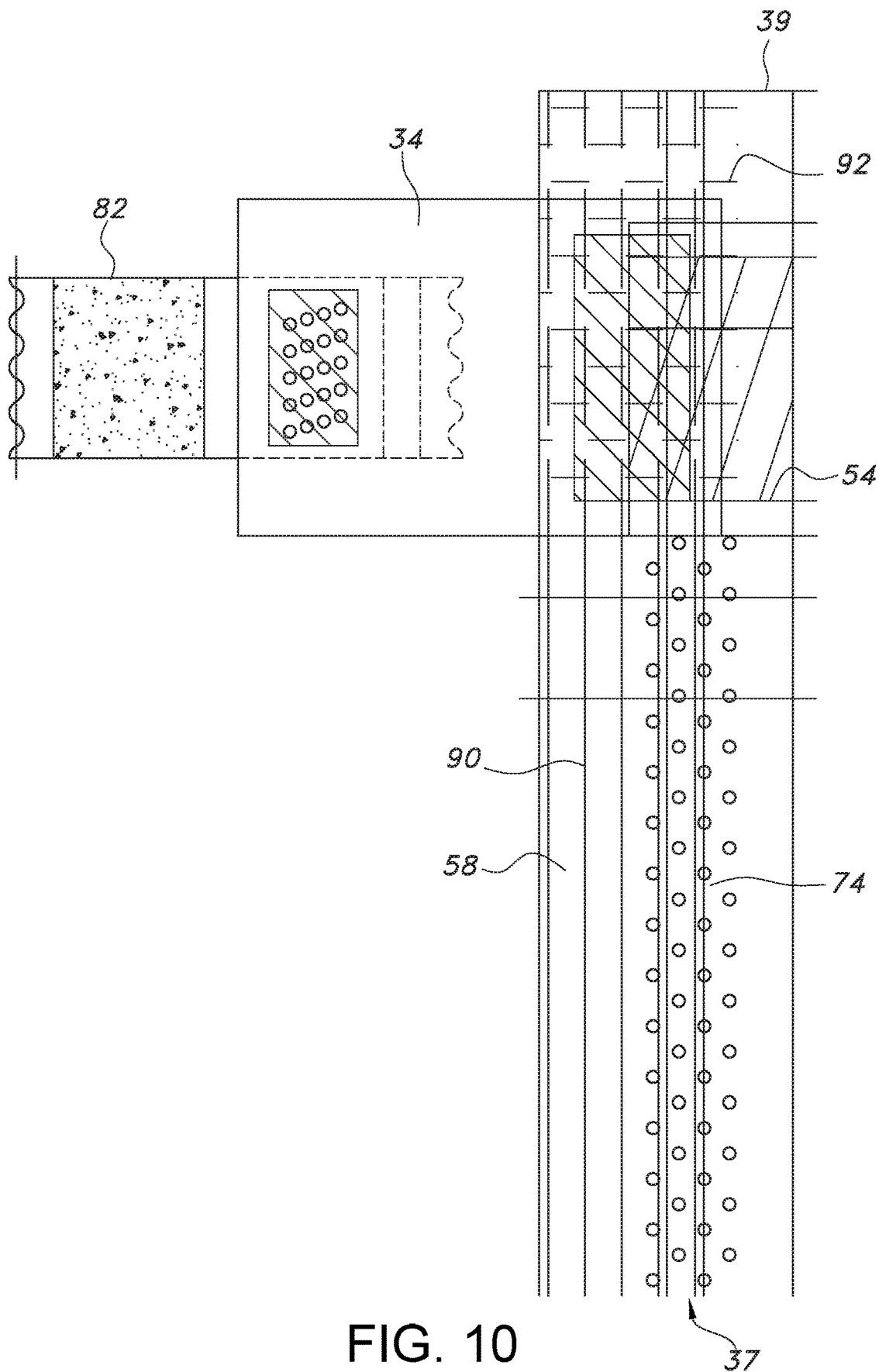
FIG. 10 is a plan view of a portion of a garment made in accordance with the present disclosure illustrating another embodiment of a vertical bonding seam for attaching components to the garment.

When the leg elastics extend from a top edge of the absorbent article to the bottom edge of the absorbent article, in one embodiment, a top portion of the leg elastics adjacent the top edge and a bottom portion of the leg elastics adjacent the bottom edge can have the elastics deadened so that the corners of the product lay flat during donning. The elastics can be deadened in any suitable manner such that the elastics are in an unstretched state. For instance, the elastics can be deadened by allowing the elastics to retract at the top portion or bottom portion of the leg elastics or by severing or chopping the elastics at the top portion and bottom portion. In one embodiment, the elastics can retract at the top portion and the bottom portion by applying the adhesive intermittently and not applying adhesive along the top portion and bottom portion of the absorbent article. In this manner, when the elastics are cut during manufacturing, the end portions of each elastic strand can retract where desired. Referring to FIGS. 8-10, different embodiments are illustrated for deadening the elastics at the top portion and at the bottom portion and for attaching the elastic side panels 34.

Referring to FIG. 8, a portion of the absorbent article 20 is shown. In particular, the leg elastic 58 is shown aligned with the longitudinal edge 37 of the chassis. At the back region of the chassis is the elastic side panel 34, which is connected to the fastening component 82. In one embodiment, the leg elastic 58 is formed by adhesively securing the plurality of elastic filaments to a web. The web may comprise a portion of the outer cover or can comprise a separate piece of material. In the embodiment illustrated in FIG. 8, the adhesive is applied to the plurality of elastic filaments in a discontinuous manner. For instance, the filaments 90 are adhesively secured to the web of material in a stretched state. The top portion and the bottom portion of the filaments 92, however, are not adhesively secured allowing for the filaments to retract and remain in an unstretched state adjacent the back waist edge 39 and at the front waist edge 38 after final cut. The filaments 92 are also in an unstretched state where the elastic side panel 34 is located. Similarly, the top portion of the leg elastic can also include elastic filaments not adhesively bonded to the web of material for also forming a portion of the leg elastic where the elastic filaments are in an unstretched state. During production of the article, the adhesive is applied discontinuously at the back region of one absorbent article and at the top region of an adjacent absorbent article. When the absorbent articles are cut to form individual products, the elastics retract as shown in FIG. 8.

As shown in FIG. 8, the elastic side panel 34 is primarily attached to the leg elastic 58. In fact, in one embodiment, the elastic side panel can only be attached to the leg elastic 58. In other embodiments, however, the elastic side panel 34 may overlap with the chassis. For instance, in addition to being attached to the leg elastic 58, the side panel 34 can also be attached to the first layer of the outer cover and/or to the second layer of the outer cover. In one embodiment, the side panel is attached to the second layer of the outer cover or the liquid impermeable film. The side panel may overlap the film a distance of greater than about 1 mm, such as greater than about 2 mm, such as greater than about 3 mm, and less than about 10 mm, such as less than about 6 mm, such as less than about 4 mm.

In one embodiment, in order to ensure that the elastic side panel 34 is securely affixed to the garment, the side panel 34 is thermally bonded or ultrasonically bonded along the vertical bonding seam 74 optionally in conjunction with adhesive bonding wherein the adhesive bonding can be continuous or intermittent. In one embodiment, a continuous mechanical bond pattern can be applied to the product in forming the vertical bonding seam 74. The vertical bonding seam and the mechanical bond pattern, for instance, may extend the entire length of the absorbent article from the top edge to the bottom edge.

In general, any suitable bonding pattern may be used. The bonding pattern, however, must be able to not only secure the elastic side panel 34 to the absorbent article but must also do so without interfering with the plurality of elastomeric strands 90.

In FIG. 8, for instance, the bond pattern that forms the vertical bonding seam 74 comprises a uniform point bonded pattern. The point bonds are spaced apart to produce enough open area that when the side panels are bonded to the absorbent article, the plurality of elastomeric strands 90 do not become trapped. For instance, in the embodiment illustrated in FIG. 8, the bond pattern comprises a plurality of point bonded columns wherein adjacent columns have the point bonds offset from one another. In one particular embodiment, for instance, the point bonds may have a diameter of from about 1 mm to about 1.7 mm, such as from about 1.2 mm to about 1.5 mm. Each column can be separated from each other a distance of from about 3 mm to about 5 mm, such as from about 3.8 mm to about 4.2 mm (from the center of the point bonds of one column to the center of the point bonds of an adjacent column). The point bonds along a single column can be spaced apart a distance of from about 3 mm to about 10 mm, such as from about 6 mm to about 7 mm. The point bonds of adjacent columns can be offset any suitable distance. In one embodiment, for instance, the point bonds of adjacent columns can be offset greater than about 0.8 mm to about 4 mm, such as from about 1 mm to about 1.5 mm. The point bond pattern can include from about 3 columns to about 8 columns, such as from about 4 columns to about 5 columns. The entire width of the bond pattern can be from about 12 mm to about 20 mm, such as from about 17 mm to about 19 mm. The above pattern not only securely affixes the side panel 34 to the garment but also does not interfere with the elastomeric strands 90.

Having the bond pattern extend the entire length of the product to form the vertical bonding seam 74 along the vertical edge 37 can provide various advantages and benefits. For instance, a continuous bond pattern tacks down all open edges of the outer cover and provides a more secure attachment to the leg elastic. The continuous bond pattern also makes the absorbent article look more seamless and aesthetically appealing.

In one embodiment, as shown in FIG. 8, the waist elastic members 54 can also overlap the side panels 34. For instance, the waist elastic member 54 can have a first end and a second and opposite end. Each end of the waist elastic member can be located along each of the opposing vertical bonding seams 74. Placing an end of the waist elastic along the vertical bonding seam 74 further reinforces the bond between the elastic side panel 34 and the garment and also reinforces the attachment of the waist elastic member 54.

Referring to FIG. 9, another embodiment of a method of forming the vertical bonding seams 74 is shown. In this embodiment, instead of a discontinuous adhesive pattern and a continuous thermal bonding pattern, the vertical bonding seam is formed by a continuous adhesive pattern and a discontinuous thermal bonding pattern. In this embodiment, an adhesive is applied along the entire length of the article. Consequently, the elastomeric strands remain in a stretched state from the top edge of the article to the bottom edge of the article. In order to deaden the elastics of the leg elastics 58 at the top portion and bottom portion of the article and in order to better secure the elastic side panels 34 to the garment, an intermittent bond pattern is applied along the vertical bonding seam 74 adjacent the top edge 39 and adjacent to the bottom edge 38 (not shown). As shown in FIG. 9, the bond pattern includes a plurality of densely spaced lateral elements that have a length that spans at least two columns of the elastic filaments 90. In this manner, the bond pattern not only securely attaches the side panel 34 and the waist elastic member 54 to the article but also chops or severs the elastic filaments 90 in order to form a portion of deadened elastics 92. The deadened elastics 92 are in an unstretched state. The leg elastic can include deadened elastomeric strands at a portion adjacent the back edge and at a portion adjacent the front edge (not shown). Severing or chopping the elastics adjacent the back edge and adjacent the front edge of the absorbent article allows for an adhesive to be applied continuously along the entire length of the vertical bonding seams.

Referring to FIG. 10, still another embodiment of a method for attaching the leg elastics 58 and the elastic side panels 34 to the absorbent article is illustrated. In FIG. 10, a continuous adhesive pattern is combined with a continuous mechanical bond pattern along the vertical bond seam 74. The continuous mechanical bond pattern, however, changes at the top portion and at the bottom portion of the leg elastic 58. More specifically, the bond pattern includes columns of point bonds as shown in FIG. 8 over the middle portion of the leg elastic 58. At the top portion of the leg elastic 58 and at the bottom portion of the leg elastic 58, however, the more dense bond pattern is used in order to deaden the elastomeric strands 92 and sever them. In the embodiment in FIG. 10, the adhesive in combination with the high density bond pattern securely affixes the side panels 34 to the garment while still deactivating elastic tension at a top portion and at a bottom portion of the leg elastic 58.

Figure 11:
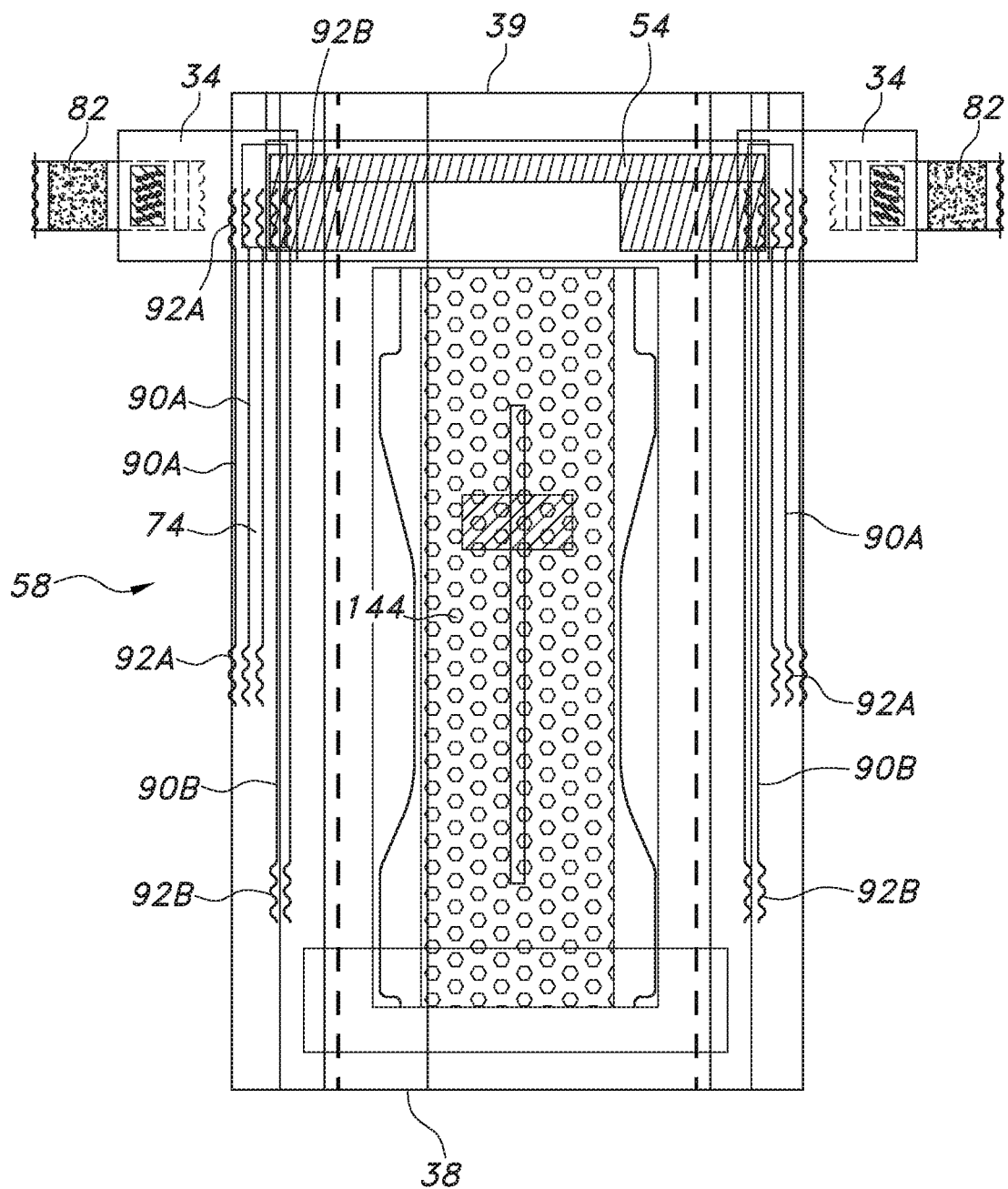
FIG. 11 is a plan view of a garment made in accordance with the present disclosure illustrating yet another embodiment of a vertical bonding seam for attaching components to the garment and to leg elastics made with elastomeric strands having differing lengths.

Referring to FIG. 11, yet another embodiment of a method for attaching the leg elastics 58 and the elastic side panels 34 to the absorbent article is illustrated. In FIG. 11, the leg elastic 58 includes elastomeric strands having offset lengths. The leg elastic 58, for instance, includes a first set of elastomeric strands 90A and a second set of elastomeric strands 90B. The elastomeric strands 90B comprise inner strands while the elastomeric strands 90A comprise outer strands such that they are positioned farthest away from the chassis. As shown, the inner elastomeric strands 90B are longer and generally extend the full length of the article in comparison to the outer elastomeric strands 90A which are shorter. More particularly, the outer strands 90A extend over the back region of the absorbent article and can extend into the crotch region. The elastomeric strands 90A, however, do not extend into the front region of the absorbent article. For instance, the outer elastomeric strands 90A can extend over from about 20% to about 70% of the length of the absorbent article, such as from about 30% to about 60% of the length of the absorbent article. Having the outermost elastomeric strands 90A only extend over a portion of the length of the absorbent article and having the elastomeric strands be positioned in the back region of the article can provide various benefits and advantages. Having offset elastomeric strands, for instance, can help shape the article in the leg area where the crotch width is narrower and can reduce the overall tension of the absorbent article. Having a narrower crotch width can reduce roping and torque that can occur as the elastomeric strands wrap around the legs of the wearer. The offset elastomeric strands may also improve the perceived rise and make the absorbent article fit closer to the body in the crotch and therefore higher on the waist. Overall, the offset elastomeric strands can produce an article having a tailored leg fit in the back region for superior BM leakage protection and also to aid in easier application and improved fit.

Applying the elastomeric strands to the article can be carried out using various methods and techniques. In one embodiment, for instance, two columns of adhesive can be applied for adhering the elastomeric strands to the leg elastics. The two columns of adhesive can also be applied discontinuously so that the end portions of each elastomeric strand retract during final cutting. For instance, elastomeric strands 90A include retracted portions 92A and elastomeric strands 90B include retracted portions 92B. The elastomeric strands retract at locations where adhesive is not applied.

In an alternative embodiment, the adhesive columns in FIG. 11 may be applied continuously and the elastomeric strands can be chopped or severed at areas 92A and 92B.

Although not shown, the embodiment in FIG. 11 can further include thermal and/or ultrasonic bonding in order to further consolidate together the different layers. For instance, the thermal or ultrasonic bonding pattern shown in FIG. 8 can also be applied along the bonding seams illustrated in FIG. 11.

Figure 12:
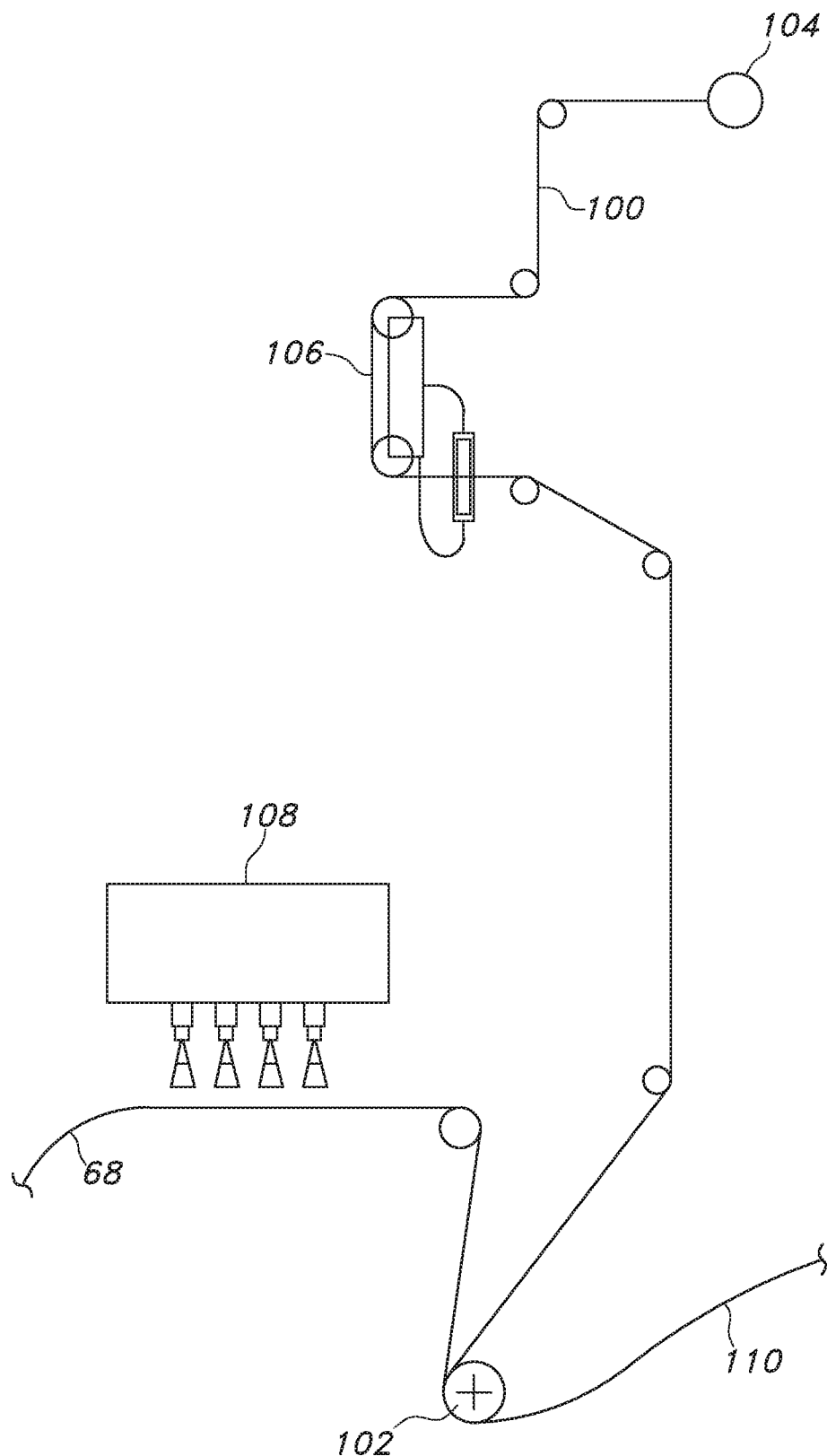
FIG. 12 is a schematic diagram illustrating one method for bonding leg elastics to a substrate for incorporation into an absorbent article in accordance with the present disclosure.
Figure 13:
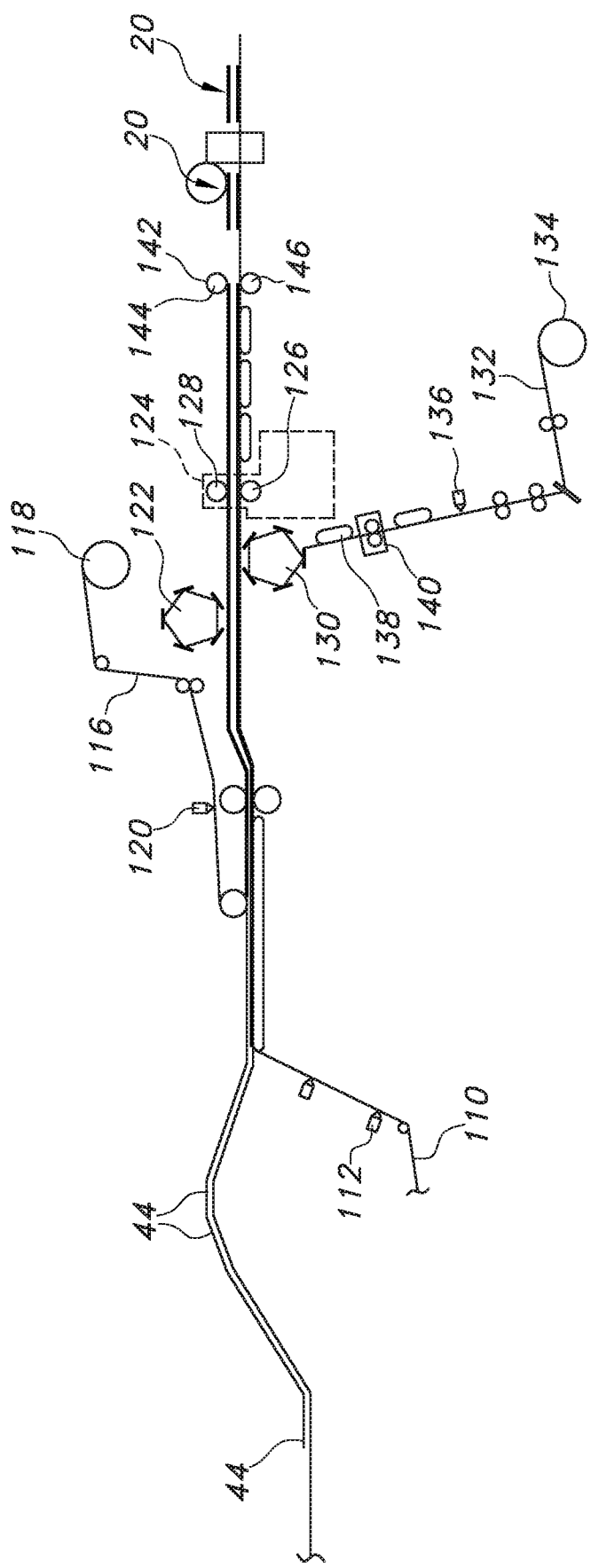
FIG. 13 is a schematic diagram of one embodiment of a method for manufacturing absorbent articles in accordance with the present disclosure.

Referring now to FIGS. 12 and 13, one embodiment of a process or method for constructing the absorbent articles in accordance with the present disclosure is shown. FIG. 12, for instance, is a schematic diagram that illustrates a method for attaching or forming one or more elastic laminate structures to a substrate, such as to a bodyside liner or an outer cover.

Referring to FIG. 12, an elastic laminate structure 68 is shown being bonded to a first substrate 100 by a bonding device 102. The elastic laminate structure 68 may comprise the elastic laminate structure illustrated in FIG. 5 or FIG. 6.

As shown in FIG. 12, the first substrate 100 is fed from a continuous roll 104 and through an in-feed web guide 106. The web guide 106 can be configured to maintain an appropriate amount of tension on the substrate 100 and/or to ensure that the substrate 100 is laterally aligned. The first substrate 100 is fed to the bonding device 102 and bonded to the elastic laminate structure 68. In the embodiment illustrated in FIG. 12, the elastic laminate structure 68 is adhesively bonded to the substrate 100 by an adhesive applicator 108. In other embodiments, however, the elastic laminate structure 68 can be bonded to the substrate 100 using a thermal bonder or an ultrasonic bonder.

In accordance with the present disclosure, two elastic laminate structures 68 are bonded to the first substrate 100 on opposite sides. The elastic laminate structure 68, for instance, may define leg elastics that are bonded to the substrate 100. In accordance with the present disclosure, the elastic laminate structures are bonded to the substrate 100 along opposite longitudinal edges such that the leg elastics extend beyond the outer edge of the substrate.

In an alternative embodiment, the elastic laminate structure 68 may comprise only elastic containment flaps. The leg elastics, on the other hand, can be formed by adhesively bonding elastic members, such as elastomeric strands along each side of the substrate as shown in FIG. 7.

As shown in FIG. 12, a composite web 110 is formed including the elastic laminate structures bonded to the first substrate.

Referring now to FIG. 13, a schematic diagram is shown illustrating one process for incorporating the composite material 110 into a plurality of discrete absorbent articles. As shown, the composite material 110 is fed into operative association with an adhesive applicator 112. The elastic laminate structure, in one embodiment, may face downward when the adhesive is applied to the substrate 100. A plurality of absorbent assemblies 44 are fed to and adhesively bonded by the adhesive to the composite material 110.

Next, a web of a second substrate 116 is bonded to the composite material 110 containing the first substrate 100. The second substrate 116 is fed from a continuous supply roll 118 and fed past an adhesive applicator 120, which applies adhesive thereto. The second substrate 116 can be adhesively bonded to the first substrate 100 of the composite material 110 so that the absorbent structures 144 are placed in between the first substrate 100 and the second substrate 116. Although FIG. 13 indicates that an adhesive is used to join the first substrate to the second substrate, it should be understood that any suitable bonding system may be utilized including thermal bonding and/or ultrasonic bonding.

As shown in FIG. 13, in one embodiment, after the two substrates are joined together, elastic side panels associated with fasteners can be attached to the formed subassembly. For example, in one embodiment, the process can include a side panel application station 122. Two opposing elastic side panels can be supplied and attached to the elastic laminate structure 68 of the composite material 110. For instance, in one embodiment, the side panels can be attached to the leg elastics that comprise a portion of the elastic laminate structure 68. The side panels can be only attached to the leg elastics at one end of the leg elastics that will later represent the back region of an absorbent article. Alternatively, the leg elastics may overlap the first substrate 100 and/or the second substrate 116. In one embodiment, for instance, the leg elastics may overlap at least one of the substrates or both substrates in an amount of less than about 10 mm, such as less than about 6 mm, such as less than about 4 mm.

As shown in FIG. 13, the process can further include a station for applying waist elastic members to the subassembly. For instance, as shown in FIG. 13, a web of elastomeric material 132 is unwound from a continuous supply roll 134 and fed past an adhesive applicator 136, which applies adhesive. The web of elastomeric material 132 is then cut into discrete elastic members 138 at a cutting station 140. The discrete elastic members 138 are then applied to the subassembly by the waist elastic applicator 130. In one embodiment, only a back waist elastic member is applied to the subassembly. In an alternative embodiment, however, both a front waist elastic member and a back waist elastic member may be applied.

The waist elastic members 138 can be adhesively bonded laterally across the formed subassembly. In one embodiment, a back waist elastic member is applied to the subassembly that includes a first end and an opposite second end. The first end can overlap with one of the elastic side panels, while the second end can overlap with the opposing elastic side panel.

After the elastic side panels and waist elastics are positioned on the subassembly, the subassembly can be fed to a thermal or ultrasonic bonding station 124. For instance, in one embodiment, the bonding station 124 can comprise a point bonding station. The point bonding station 124 includes a patterned roll 126 opposite an anvil roll 128. In one embodiment, the patterned roll 126 is heated and includes a plurality of raised landing portions. The raised portions of the patterned roll 126 thermally bond the components of the subassembly together.

The adhesive applicator 108 as shown in FIG. 12 in conjunction with the point bonding station 124 illustrated in FIG. 13 can operate in conjunction in order to form two opposing and parallel vertical bonding seams along the moving subassembly as shown in FIG. 13. In particular, the adhesive applicator 108 and the point bonding station 124 can be used to create the different vertical bonding seam configurations shown in FIGS. 8-10.

For instance, in the configuration in FIG. 8, the adhesive applicator 108 applies a discontinuous pattern to the elastic laminate structure 68 such that the elastic laminate structure is not adhered to the substrate at locations that later represent the top portion and the bottom portion of the chassis of the absorbent article. The point bonding station 124, on the other hand, then applies a continuous point bonding pattern that is also uniform. As shown in FIG. 8, for instance, the point bonding pattern can include a plurality of point bonds in offset columns that are designed to bond together each layer of material including the leg elastics, the elastic side panels, and any overlap with the first substrate and/or the second substrate. The point bonds can also bond one end of the waist elastic to the subassembly. In FIG. 8, the point bond pattern is specifically designed so as to not interfere with elastomeric strands contained in the leg elastics. By not adhesively bonding the leg elastics at the top portion and bottom portion of the chassis, the leg elastics retract when the subassembly is cut into individual absorbent articles.

In FIG. 9, the adhesive applicator 108 applies a continuous column of adhesive on the substrate, while the point bonding station 124 applies a discontinuous bonding pattern. The point bonding station 124, for instance, can apply high density point bonds in the form of transverse elongated elements at the top portion and back portion of each leg elastic contained in the subassembly. In this manner, the point bonds serve two purposes. First, the point bonds attach the waist elastic and the leg elastic to an elastic side panel. The waist elastic and elastic side panel is also bonded to the first and/or the second substrate to the extent that they overlap. In addition to bonding the different components together, the bonding pattern also deadens the elastic within the leg elastics at the top portion and bottom portion.

In the embodiment of FIG. 10, on the other hand, both the adhesive applicator 108 and the point bonding station 124 apply continuous adhesive and continuous point bonds over the entire length of the vertical bonding seam. The point bonding pattern, however, is non-uniform and includes high density point bonds at a bottom portion of the elastic and at a top portion of the elastic and includes spaced apart low density point bonds along a middle portion of the leg elastic. In this manner, the point bonding station creates a consolidated structure while also deadening the elastics at the top portion and bottom portion without also interfering with the elastics within the middle portion of each leg elastic.

In one embodiment, the elastic members contained in the elastic components, such as contained in the elastic side panels, the leg elastics and the waist elastic members can be heat activated. Exposing the elastic members to heat, for instance, can cause the elastic members to gather.

As shown in FIG. 13, the subassembly after the point bonding station 124 is fed to a cutter assembly 142 that divides the subassembly into discrete absorbent articles 20. The cutter assembly 142 can include a knife roll 144 opposite an anvil roll 146 that is configured to cut the subassembly into the individual absorbent articles. Downstream from the cutter assembly 142, can be folded and packaged for distribution to consumers.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A method of manufacturing an absorbent article comprising:
    forming a first leg elastic along a first longitudinal edge of a moving first substrate and forming a second leg elastic along a second and opposite longitudinal edge of the moving first substrate, each leg elastic comprising an elastic member, the first leg elastic extending outboard of the first longitudinal edge of the first substrate and the second leg elastic extending outboard of the second longitudinal edge of the first substrate;
    joining a first side panel to the first leg elastic and joining a second side panel to the second leg elastic, the first side panel being associated with a first fastening device and the second side panel being associated with a second fastening device;
    attaching a plurality of absorbent assemblies to the first substrate;
    joining a second substrate to the first substrate such that the absorbent assemblies are positioned between the first substrate and the second substrate and a subassembly is formed; and
    cutting the subassembly into a plurality of discrete absorbent articles.

2. A method as defined in claim 1, wherein the first substrate comprises a bodyside liner of the absorbent article and the second substrate comprises the outer cover of the absorbent article.

3. A method as defined in claim 1, wherein the first substrate comprises an outer cover of the absorbent article and the second substrate comprises a bodyside liner of the absorbent article.

4. A method as defined in claim 1, wherein the first leg elastic is attached to the first substrate along a first vertical bonding seam, the first leg elastic extending from a top edge to a bottom edge of the absorbent article, the second leg elastic attached to the first substrate along a second vertical bonding seam, the second leg elastic extending from the top edge to the bottom edge of the absorbent article.

5. A method as defined in claim 4, wherein the first leg elastic comprises an elastic laminate structure containing a plurality of elastomeric strands, and wherein the first leg elastic includes a top portion adjacent the top edge and a bottom portion adjacent the bottom edge of the absorbent article and wherein the elastomeric strands have been deadened in the top portion and in the bottom portion of the first leg elastic, the second leg elastic also comprising an elastic laminate structure containing a plurality of elastomeric strands, and wherein the second leg elastic includes a top portion adjacent the top edge and a bottom portion adjacent the bottom edge of the absorbent article and wherein the elastomeric strands within the top portion and the bottom portion of the second leg elastic have been deadened.

6. A method as defined in claim 5, wherein the top and bottom portions of the leg elastics have been deadened by retracting the elastomeric strands, severing the elastomeric strands, or both retracting and severing the elastomeric strands.

7. A method as defined in claim 4, wherein the first side panel is attached to the absorbent article along the first vertical bonding seam and the second side panel is attached to the absorbent article along the second vertical bonding seam.

8. A method as defined in claim 7, further comprising the step of attaching a first elastic containment flap along the first vertical bonding seam and attaching a second elastic containment flap along the second vertical bonding seam.

9. A method as defined in claim 7, further comprising the step of attaching a waist elastic member to the absorbent article, the waist elastic member including a first end and a second and opposite end, the first end being attached along the first vertical bonding seam and the second end being attached along the second vertical bonding seam.

10. A method as defined in claim 9, wherein the first end of the waist elastic member overlaps the first side panel and the second end of the second waist elastic member overlaps the second side panel.

11. A method as defined in claim 4, wherein the first vertical bonding seam is formed by applying a thermal point bonding pattern along the first longitudinal edge and the second vertical bonding seam is formed by applying a thermal point bonding pattern along the second longitudinal edge.

12. A method as defined in claim 11, wherein the first vertical bonding seam is also formed by applying an adhesive along the first longitudinal edge and the second vertical bonding seam is formed by applying an adhesive along the second longitudinal edge.

13. A method as defined in claim 11, wherein each vertical bonding seam comprises a plurality of columns of offset bond points that extend from a top edge to a bottom edge of the absorbent article.

14. A method as defined in claim 11, wherein the vertical bonding seams each comprise a column of bond points and wherein the bond points have a higher density over the side panels.

15. A method as defined in claim 14, wherein the density of the bond points over the side panels is sufficient to destroy the elasticity of the leg elastic.

16. A method as defined in claim 1, wherein the first leg elastic is formed by enclosing a plurality of elastomeric strands in the first substrate or in the second substrate along the first vertical edge and the second leg elastic is formed by enclosing a plurality of elastomeric strands in the first substrate or the second substrate along the second longitudinal edge.

17. A method as defined in claim 1, wherein the first substrate, the second substrate, and the absorbent assembly positioned between the first substrate and the second substrate form a chassis of the absorbent article and wherein the first leg elastic is formed by enclosing a first plurality of elastomeric strands in a first web material to form a first elastic laminate structure and attaching the first elastic laminate structure to the chassis and wherein the second leg elastic is formed by enclosing a first plurality of elastomeric strands in a first web material to form a second elastic laminate structure and attaching the second elastic laminate structure to the chassis.

18. A method as defined in claim 17, wherein each elastic laminate structure further comprises a second plurality of elastomeric strands spaced from the first plurality of elastomeric strands, the first plurality of elastomeric strands forming the leg elastics and the second plurality of elastomeric strands forming respective first and second elastic containment flaps.

19. A method as defined in claim 18, wherein the first plurality of elastomeric strands and the second plurality of elastomeric strands are enclosed within a single web of material to form the respective elastic laminate structures.

20. A method as defined in claim 18, wherein the first plurality of elastomeric strands are enclosed within a first web of material and the second plurality of elastomeric strands are enclosed in a second web of material to form each respective elastic laminate structure.

21. A method as defined in claim 7, wherein the absorbent article defines a chassis and wherein the first side panel is attached to the first leg elastic and the second side panel is attached to the second leg elastic and wherein each side panel overlaps the chassis by less than 6 mm.

22. A method of manufacturing absorbent articles comprising:
    forming a chassis by enclosing an absorbent structure in between a bodyside liner and an outer cover material, the chassis including a first longitudinal edge spaced from a second longitudinal edge that extend from a top edge of the chassis to a bottom edge of the chassis;
    attaching a first leg elastic along the first longitudinal edge of the chassis to form a first vertical bond seam and attaching a second leg elastic along a second longitudinal edge to form a second longitudinal bond seam, each longitudinal bond seam extending from the top edge to the bottom edge of the chassis wherein the first leg elastic extends outboard of the first longitudinal edge of the chassis and the second leg elastic extends outboard of the second longitudinal edge of the chassis;
    attaching a first side panel to the first leg elastic adjacent the bottom edge when forming the first longitudinal bond seam and attaching a second side panel to the second leg elastic adjacent the bottom edge when forming the second longitudinal bond seam; and
    deadening the elasticity of each leg elastic along a top portion of each leg elastic adjacent the top edge and along a bottom portion of each leg elastic adjacent the bottom edge.

* * * * *

UNITED STATES PATENT AND TRADEMARK OFFICE
CERTIFICATE OF CORRECTION

PATENT NO. : 12,059,332 B2  
APPLICATION NO. : 16/489011  
DATED : August 13, 2024  
INVENTOR(S) : David J. Enz et al.

Page 1 of 1

It is certified that error appears in the above-identified patent and that said Letters Patent is hereby corrected as shown below:

On the Title Page

Column 1, Under Item (72) Inventors "David J. Enz, Neenah, WI (US); James P. King, Farr West, UT (US); Sarah A. Kleuskens, Neenah, WI (US); Pat Abney, Menasha, WI (US); Kevin Dolan, Pine River, WI (US); Qianxiang Feng, Neenah, WI (US); Andrew T. Hammond, Grand Chute, WI (US)" should read --David J. Enz, Neenah, WI (US); James P. King, Farr West, UT (US); Sarah A. Kleuskens, Neenah, WI (US); Pat Abney, Menasha, WI (US); Kevin Dolan, Pine River, WI (US); Qingxiang Feng, Neenah, WI (US); Andrew T. Hammond, Grand Chute, WI (US)--

Signed and Sealed this  
Tenth Day of September, 2024

Katherine Kelly Vidal  
*Director of the United States Patent and Trademark Office*